(12) United States Patent
Tukker

(10) Patent No.: US 6,806,959 B2
(45) Date of Patent: Oct. 19, 2004

(54) MEASUREMENT OF SURFACE DEFECTS ON A MOVABLE SURFACE

(75) Inventor: Teunis Willem Tukker, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 62 days.

(21) Appl. No.: 09/990,215

(22) Filed: Nov. 21, 2001

(65) Prior Publication Data

US 2002/0080363 A1 Jun. 27, 2002

(30) Foreign Application Priority Data

Nov. 22, 2000 (EP) .............................................. 00204124

(51) Int. Cl.[7] .................................................. G01B 9/02
(52) U.S. Cl. ..................................................... 356/484
(58) Field of Search ............................... 356/28.5, 484, 356/485, 491, 492, 496, 500, 511, 512

(56) References Cited

U.S. PATENT DOCUMENTS

| | | | |
|---|---|---|---|
| 5,825,465 A | 10/1998 | Nerin et al. ............... | 356/28.5 |
| 5,861,952 A * | 1/1999 | Tsuji et al. ................. | 356/484 |
| 5,898,499 A * | 4/1999 | Pressesky .................... | 356/450 |
| 5,923,423 A | 7/1999 | Sawatari et al. ............ | 356/349 |
| 6,317,216 B1 * | 11/2001 | Maris .......................... | 356/496 |

* cited by examiner

Primary Examiner—Samuel A. Turner
Assistant Examiner—Michael A. Lyons
(74) Attorney, Agent, or Firm—Aaron Waxler

(57) ABSTRACT

A device for the inspection of one or more movable surfaces (8), more in particular for the inspection of a rotating surface (8) of a wafer, which device includes at least one light source (1), notably a laser light source, and a beam splitter (4) for splitting a light beam that is emitted by said laser light source into at least one reference beam (6) that is applied to a detector (16) and at least one measuring beam (5) that is applied to the surface (surfaces) and contains at least one component in the direction of movement (U) of the respective surface or in the opposite direction, the light (15) that is reflected by the surface (8) having, upon detection of a defect (14), a frequency ($\upsilon'$) that has been shifted relative to the measuring beam (5) and on which the reference beam (6) can be superposed. The device includes an evaluation unit (29) for determining the velocity (v) of a defect (14) on the surface (8) from the shifted frequency ($\upsilon'$) and for determining the position of the defect on the surface therefrom.

13 Claims, 3 Drawing Sheets

MEASUREMENT OF SURFACE DEFECTS ON A MOVABLE SURFACE

Figure 1:
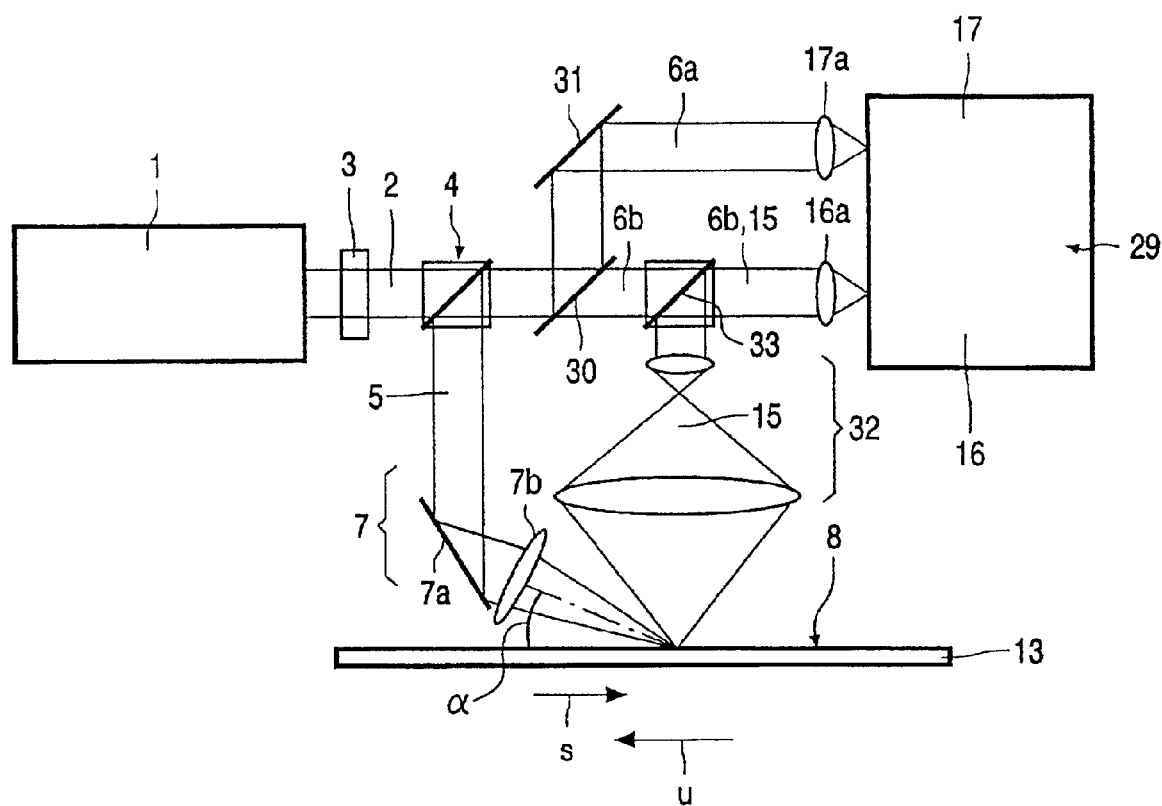

The invention relates to a device for the inspection of surfaces as disclosed in the introductory part of claim 1, and to a method as disclosed in the introductory part of claim 13.

U.S. Pat. No. 5,923,423 teaches the use of a device for the inspection of surfaces which includes a laser light source whose emitted beam is first split into two sub-beams in a beam splitter, one sub-beam being applied to a photodetector as a reference beam whereas the other beam is applied to the surface to be inspected as a measuring beam. The measuring beam has a direction which essentially opposes that of the surface movement. The light reflected by the surface is superposed on the reference beam in the further optical beam path (heterodyne detection). A space resolution detector (an array of, for example, photodiodes) provides the localization of surface defects on the surface. This requires very accurate adjustment of the detector relative to the surface. The resolution is limited by the detector, for example a CCD camera.

It is an object of the invention to enhance the measurement of contaminations or damage on surfaces.

The object is achieved in accordance with the invention by means of a device that includes an evaluation unit for determining the velocity (v) of a defect on the surface from the shifted frequency (v') and from this velocity the position of the defect on the surface, by means of a method where the speed of a defect on the surface is determined from the superposed signal formed from the at least one reference beam and the reflected light, and that the position of the defect on the surface is determined therefrom, and by means of an evaluation unit with a computer program that determines the frequency of the input signal from an alternating voltage component thereof, compares this frequency with a reference and calculates therefrom, by way of the Doppler formula, the velocity that corresponds to the frequency difference between said signals.

Because of the construction of the device in accordance with the invention, in which a detected defect is localized by way of a Doppler frequency shift, a speed that is determined therefrom, and an arithmetical determination of the position that is thus enabled, the location can be very accurately determined. This results in a very high resolution of the device that also enables the detection of small defects. Moreover, the speed of measurement is very high.

Defects occurring on the surface (for example, a particle resting thereon or a damage area that extends inwards (pinhole)), are irradiated in motion by the component of the light beam that extends in the direction thereof or in the opposite direction, so that the frequency of the light that is reflected by the defect is changed relative to that of the applied light. The use of the Doppler effect significantly simplifies the measurement of the location. The detector need not satisfy very severe requirements. Moreover, the laser need not oscillate in a defined mode either. The frequency shift that is induced between the applied light and the reflected light by the speed of the defect lies in the range that can be readily measured, that is, typically in a range of the order of magnitude of a few 10 kHz, thus facilitating the evaluation.

The resolution is significantly finer than the size of the light spot. Therefore, despite the desired high resolution a comparatively large light spot can be used so that the time required for scanning the surface is reduced.

When an elliptical light spot is formed with a major axis that extends radially in the case of a round or practically round wafer to be inspected, defects in different radial positions on the surface to be inspected will traverse different regions of the light spot. Because the defects that are situated further outwards in the radial direction have to travel a distance per unit of time that is larger than that traveled by defects that are situated further inwards, their speed is increased; this increase can be measured by way of the Doppler shift of the frequency. The radial position of the defect can thus be localized. The invention thus enables exact determination of the position of a detected defect by way of a velocity measurement that is carried out on the basis of the Doppler frequency shift.

There is also envisaged detection of the instantaneous orientation of the surface, for example, in a decoder associated with the rotary drive of the wafer, so that additionally, for example, the angular position of a wafer can be determined upon detection of a defect. The pole co-ordinates of the defect are thus fully known. Exact localization is then possible.

Figure 2:
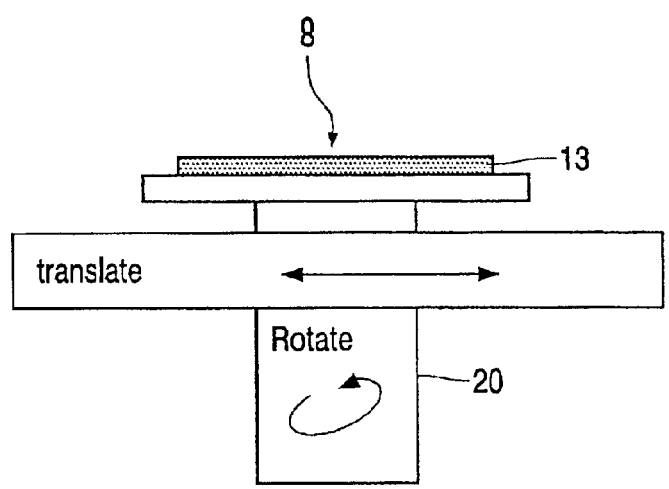
Figure 3:
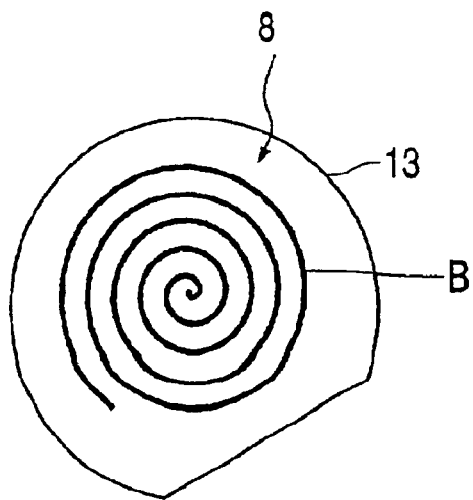
Figure 4:
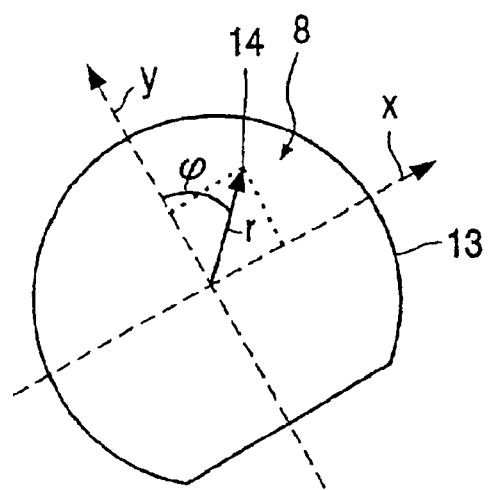
Figure 5:
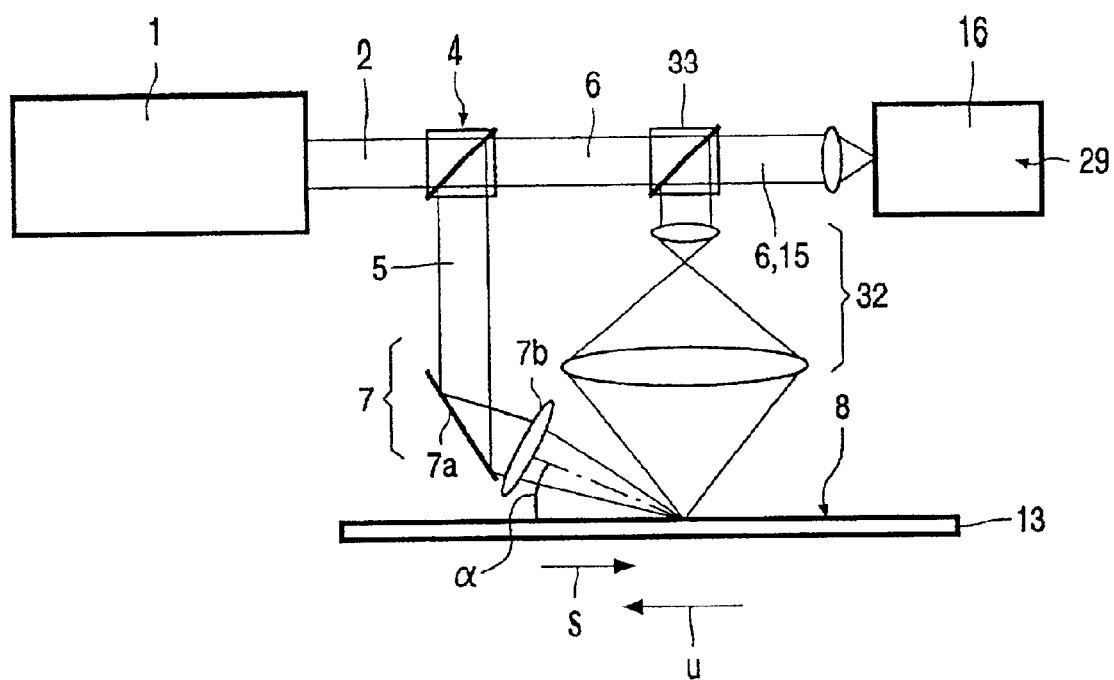
Figure 6:
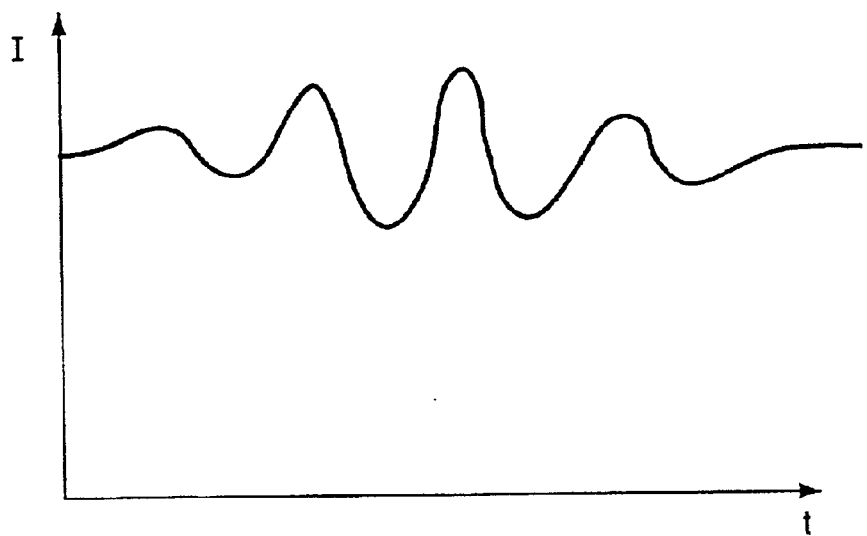

Further advantages and details of the invention will become apparent from the embodiments of the invention that are described in detail hereinafter with reference to the drawing. In the drawing:

FIG. 1 is a diagrammatic overall representation of a first embodiment of a device in accordance with the invention, FIG. 2 is a side elevation of a sample holder, FIG. 3 is a plan view of the surface to be inspected in which the trajectory of the sample is also indicated, FIG. 4 is a view similar to that of FIG. 3 with inserted cartesian and pole co-ordinates of a surface defect, FIG. 5 is a diagrammatic overall representation of a second embodiment of a device in accordance with the invention, and FIG. 6 shows as a function of time the measuring signal that is formed in the device shown in FIG. 5.

The embodiment of the device that is shown in FIG. 1 includes a light source 1 which is preferably constructed as a laser light source because of the desired monochromaticity and the high intensity. However, the use of a laser light source is not absolutely necessary, since a beam splitter 4 that is arranged in the emitted beam 2 could also lead to interference of beams 5 and 6 split off from the original beam 2, that is, even in the case of light rays of small coherence length only while the path is the same. FIG. 1 shows different path lengths of the reference beam 6 on the one side and the path length of the beam that acts on the surface 8 and of the light 15 deflected by this surface or by a defect 14 on the other side. In order to make interference of the reflected light 15 with the reference beam 6 also possible in such a case, long coherence lengths are required; such lengths are offered by a laser.

The laser 1 continuously emits monochromatic light, that is, approximately in the visible range and typically of a wavelength of, for example, 488 nm. Even though use can be made of a light source with a shorter wavelength so as to improve the sensitivity, the scatter cross-section of the light with the air surrounding the surface then also increases. Granted, measurement in a helium atmosphere or in vacuum conditions is also possible in theory, but would be very expensive.

A beam splitter 4 is arranged in the beam path of the beam emitted by the laser 1. The beam splitter may be constructed in various ways, for example as Fresnel's mirrors, as a double gap, as a combination of a polarizing optical cube and a λ/2 plate, or as another known mechanism. In the present embodiment the light beam 2 is split into two beams 5, 6 only. However, it is also possible to split off further measuring beams 5 and to inspect, for example, a plurality of surfaces 8 simultaneously.

A semi-transparent mirror which constitutes a very simple and inexpensive component is used as the beam splitter 4 in the present embodiment.

The beam splitter 4 may be preceded by an optical system 3, for example a telescope with two cylindrical lenses. Magnification by the optical system 3 takes place in one plane only. The telescope 3 ensures that the beam splitter is uniformly illuminated within an essentially elliptical region, so that the light spot 9 arising beyond this region also has an elliptical contour; such an elliptical light spot extends in the radial direction of a round wafer 13 to be inspected and such a wafer could be provided with a cut-out to enhance the ease of handling.

The measuring beam 5 that is separated from the light beam 2 by the beam splitter 4 is applied to a further optical system 7 which includes a deflection mirror 7a and a focusing optical system 7b, for example a converging lens. Alternatively, or additionally to the lens 3, the converging lens 7 may also have a cylindrical construction in order to realize an elliptical light spot 9 on the surface 8. The optical system 7 applies the measuring beam 5 in a tangential direction at a flat angle of incidence α to the rotating surface 8 of the wafer 13 to be inspected, notably a silicon wafer that is provided with a coating or not, for example, a wafer for an optically and/or magnetically readable data carrier, thus forming a light spot 9 on this surface. In the present embodiment the beam is applied with a component S in the direction opposing the direction of rotation U of the wafer 13. Application with a component in the direction of rotation U is also possible.

The light spot 9 can be moved by means of a movable optical system, that is, in this case in the radial direction of the wafer 13 to be inspected, thus enabling complete scanning of the surface 8 thereof. It is particularly advantageous to keep the entire optical system that influences the incident beam 2 stationary instead and to make the wafer 13 perform, in addition to the rotary movement, a superposed translatory movement so that the spiral-like trajectory B of the object 13 as shown in FIG. 3 is obtained. The light spot 9 retains its position and the wafer 13 is moved underneath the light spot in such a manner that its surface 8 can be completely scanned.

In a first embodiment (FIG. 1) the reference beam 6 that is also formed in the beam splitter 4 from the beam 2 emitted by the light source 1 is applied without deflection (be it that this is not an absolute condition) to a semi-transparent mirror 30 in which a part 6a of the reference beam 6 is deflected and a further part 6b is rectilinearly applied to an entrance window of a detector 16.

The part 6a of the reference beam that is deflected by reflection in the mirror 30 is applied, via a further mirror 31, to an entrance window of a second detector 17 which may also be integrated with the first detector 16 so as to form one unit. Each of the entrance windows is preceded by a respective collimating optical system 16a, 17a that is shown in the form of a converging lens in the drawing.

The circular frequency ω of the inspected surface 8 is constant; therefore, any defects 14 present are passed underneath the light spot 9, that is, in the direction transversely of the major axis thereof, at a constant circular frequency ω. Depending on the radial position of a defect 14, its speed of revolution differs, because for a particle that is situated further outwards the speed of revolution $$v = \omega r$$

(where r=radial distance between the defect 14 and the center) is higher than for a defect that is situated further inwards.

The sample 13 is mounted on a sample holder 20. With the sample holder there is associated a decoder for detecting its instantaneous position, in this case being an angular position. When a defect 14 occurs, the relevant angle of rotation of the sample holder 20 can thus be determined upon the passage of the defect 14 through the light spot 9.

When a defect 14 occurs on the surface 8, the measuring beam 5 is scattered thereby. The scattered light 15 is imaged, via an optical mirror system 32, in the mirror 33 so as to be superposed with the reference beam 6, resulting in a time-modulated signal (FIG. 6) with a constant component from the reference beam 6 and a temporally periodic component from the reflected light 15. The optical system 32 should not have an excessively large numerical aperture, because the Doppler frequency shift is dependent on the scatter angle. If the scatter cone detected is too large, therefore, a significant widening of the measured frequency occurs. The reflected light 15, superposed on the reference beam 6b, is applied to the entrance gap of the first light-sensitive detector 16 by way of the optical system 16a. The reference beam 6a is applied to the second detector 17. The detector 16, or the detectors 16, 17, need not detect in a space resolved mode. The noise of the laser, formed from the reference beam 6 and detected by the detector 17, can be subtracted by comparison of the input signals of the detector 16 and the detector 17. Only the temporally modulated component then remains for evaluation; this results in a distinct signal waveform. A component of this kind, comprising the detectors 16, 17, is also referred to as a noise cancellation detector.

Because the superposed signal of the reflected light 15 and the reference beam 6b is modulated with the difference frequency resulting from the Doppler shift in the case of occurrence of a defect 14, the acquisition of the measuring signal may also be such that only signals that have the appropriate frequency are evaluated. For example, signals that are due to scatter on air and do not have this frequency are thus filtered out. The measuring window can be pre-adjusted in such a manner that it has limit frequencies in the form of difference frequencies that correspond to the maximum outer position of a defect 14 on the wafer 13 and difference frequencies that correspond to the maximum inner position of the defect 14 on the wafer 13.

It will be evident that the light source 1, the surface 8 and the detectors 16, 17 can be arranged in a variety of ways that can be realized by selection of suitable deflection and converging optical systems. It is not necessary either, of course, that the light 2 is incident on the surface 8 from above; it may also be directed downwards or be oriented in a different way. The detector 16 or the detectors 16, 17 are constructed as photoelectric detectors in known manner and hence convert a light signal into an electrical signal. Typically photodiodes can be used in the detectors 16, 17.

A second embodiment (FIG. 5) is provided with only one detector 16 in which a superposed signal from the reference beam 6 and the reflected light 15 is detected; this results in the signal that is shown in FIG. 6 and that also constitutes the input signal for the detector 16 in the above version. As opposed to the first embodiment, however, no second detector 17 is provided for a reference beam 6a, so that no background suppression takes place in the detector 16. The time modulation of the signal, however, can be distinguished so that the frequency shift can be derived therefrom.

The function of the device 1 and the method in accordance with the invention will be explained on the basis of FIG. 1.

The measuring beam 5 that is formed in the beam splitter 4 is incident on the surface 8 within the light spot 9 that remains constant during the entire measurement.

In the case of an ideally smooth surface 8, the light is reflected (except for the scattering on air molecules) subject to the reflection condition: angle of incidence=angle of exit. The light thus reflected is not incident on any of the entrance windows of the detector 16 or the detectors 16, 17. However, the detector 16 or 17 always receives a signal from the reference beam 6 or 6a or 6b.

When a defect 14 occurs, the incident light 2 is scattered thereby. The scattered light 15 can be detected by way of the detector 16.

The position of the defect 14 on the surface can be very accurately determined even in the case of a stretched light spot 9, for example a light spot 9 that is elliptically stretched in such a manner that its major dimension extends radially with respect to the wafer; this is a central aspect of the invention: from the setting of the optical system that guides the light beam 2 it is known where this beam is incident on the rotating wafer 13, that is, where the strip that is scanned by the light spot 9 is situated in the radial direction. When a signal occurs in a detector 16, the instantaneous angular position of the sample holder 20 is determined by way of the decoder.

To this end, the sample holder may be provided, for example, with an angular scale which is automatically read, by way of the decoder, at the instant of reception of a signal by at least one of the detectors 16, 17. Consequently, the angle of rotation φ of the sample holder 20 with the wafer 13 that is arranged so as to be stationary thereon is known. In order to enable the determination also of the radial distance r as a second pole co-ordinate, the Doppler frequency shift of the reflected scattered light 15 relative to the applied measuring beam 5 is determined. For applied light in the visible range (wavelength λ of the order of magnitude of $10^{-7}$ m) it has a frequency ν of the order of magnitude of $10^{15}$ Hz in conformity with the formula:

$$\nu = c/\lambda$$

(where c=velocity of light ($3 \ast 10^8$ m/s)).

This frequency value cannot be detected as an absolute value in a detector. Consequently, the frequency ν' of the scattered light 15, having been shifted only slightly with the respect to the incident measuring beam 5, cannot be determined as an absolute value either. The shifted frequency ν' is calculated such that instead of the wavelength λ=c/ν a shifted wavelength $$\lambda' = (c-v)/\nu$$

(where v=velocity of the defect 14 that is subject to the measuring beam 5, multiplied by sin α, FIG. 1, FIG. 5) must be applied; therefrom the following formula is obtained for the shifted frequency ν':

$$\nu' = c/((c-v)/\nu) = \nu/(1-v/c).$$

However, because v<<c, the frequency variation is very small; it is typically in the range of kHz or 10 kHz. The frequency variation can thus be easily measured.

Because of the superposition of the reference beam 6 that oscillates at the original frequency ν and the reflected light 15 that oscillates at the shifted frequency ν', the difference between the two frequencies, that is, the so-called Doppler shift, is impressed as a modulation on the measured signal. The particle velocity v can be calculated therefrom by way of the above formula. Because the circular frequency ω of the rotating surface 8 is known, the radial distance r between the defect 14 and the center can be calculated from $$v = \omega r$$

Because the angular frequency ω is constant, for the purpose of checking the member 13 can also be rotated a number of times for measurement in order to determine therefrom a mean value with a standard deviation. An error calculation can then be performed. A very high accuracy is thus achieved in the determination of the position of the defect 14.

It will be evident that the device in accordance with the invention is not only suitable for the inspection of wafers 13, but also for the inspection of arbitrary other semiconductor surfaces or other surfaces, for example, substrates with thin layers, surfaces of optical or magnetic storage media, CDs, DVDs, and masks for the application of semiconductor structures, etc.

What is claimed is:

1. A device for the inspection of a rotating surface (8) of a wafer (13), which device includes at least one light source (1), and a beam splitter (4) for splitting a light beam (2) that is emitted by said source into at least one reference beam (6) that is applied to a detector (16) and at least one measuring beam (5) that is applied to the surface (surfaces), the at least one measuring beam (5) containing at least one component in the direction of movement (U) of the relevant surface (8) or in the opposite direction, and the light (15) that is reflected by the surface (8) having, at least upon detection of a defect (14) on the surface (8), a frequency (ν') that has been shifted relative to th at least one measuring beam (5) and that the at least one reference beam (6) can be superposed thereon, characterized in that the device includes an evaluation unit (29) for determining the velocity (v) of a defect (14) on the surface (8) from the shifted frequency (ν') and from this velocity the position of the defect on the surface (8).

2. A device as claimed in claim 1, characterized in that the detector (16) has exactly one entrance window that is capable of detecting the superposition of the reference beam (6) and the reflected light (15).

3. A device as claimed in claim 1, characterized in that there are provided two detectors (16; 17), the reference beam (6) being detectable by a first detector whereas the superposition of the reference beam (6) and the light (15) can be detected by a second detector.

4. A device as claimed in claim 1, characterized in that the superposition of the reference beam (6) and the reflected light (15) is formed in an optical beam path and that the superposition image thus obtained can be projected into an entrance window of a detector (16).

5. A device as claimed in claim 1, characterized in that the input signal formed by the superposition of the reference beam (6) and the reflected light (15) can be electronically evaluated and that a frequency shift (ν-ν') of the reflected light (15) can be determined therefrom.

6. A device as claimed in claim 1, characterized in that the velocity of rotation (v) of a rotating defect (14) can be calculated from to the frequency shift (ν-ν') by way of the Doppler formula.

7. A device as claimed in claim 6, characterized in that a radial position (r) of the defect (14) can be calculated from the velocity (v) of the defect (14) while a circular frequency (ω) of the rotation of the surface (8) is known.

8. A device as claimed in claim 1, characterized in that a moving surface (8) is associated with a device for detecting its instantaneous orientation.

9. A device as claimed in claim 7, characterized in that the surface (8) is rotatable in the plane in which its major axis extends and that the device enables detection of the angle of rotation.

10. A device as claimed in claim 4, characterized in that the position of a defect (14) on the inspected surface relative to a scale can be determined from the signal detected by the detector (16; 17).

11. A device as claimed in claim 1, characterized in that the surface (8) to be inspected can move in a rotational as well as in a translational mode.

12. A method for the inspection of one or more moving surfaces, where a light beam that is emitted by a light source, is split by means of a beam splitter into at least one reference beam that is applied to a detector and a measuring beam that is applied to the surface, the measuring beam containing at least one component in the direction of movement of the relevant surface or in the opposite direction, the light that is reflected by the surface having, at least upon detection of a defect on the surface, a frequency that has been shifted relative to the measuring beam, and the at least one reference beam being superposed on said reflected light, characterized in that the speed of a defect on the surface is determined from the superposed signal formed from the at least one reference beam and the reflected light, and that the position of the defect on the surface is determined therefrom.

13. An evaluation unit (29) for evaluating at least one electrical input signal which contains an alternating voltage component, the evaluation unit storing a computer program, that is, notably a program for carrying out the method in conformity with claim 12, characterized in that the computer program determines the frequency of the input signal from an alternating voltage component thereof, compares this frequency with a reference and calculates therefrom, by way of the Doppler formula, the velocity that corresponds to the frequency difference between said signals.

* * * * *